United States Patent [19]
Chan et al.

[11] Patent Number: 5,139,491
[45] Date of Patent: Aug. 18, 1992

[54] 2-DECARBOXYL-2-ALKOXYALKYL PROSTAGLANDINS AS OCULAR HYPOTENSIVES

[75] Inventors: Ming F. Chan, Lake Bluff, Ill.; David F. Woodward, El Toro, Calif.

[73] Assignee: Allergan, Inc., Irvine, Calif.

[21] Appl. No.: 623,234

[22] Filed: Dec. 6, 1990

[51] Int. Cl.$^5$ ............................................. A61M 35/00
[52] U.S. Cl. ................................... 604/294; 604/298; 424/427; 514/573; 514/913
[58] Field of Search ................. 604/294, 298; 424/427; 514/913, 573

[56] References Cited

U.S. PATENT DOCUMENTS

| | | | |
|---|---|---|---|
| 4,256,745 | 3/1981 | Skuballa et al. | 514/530 |
| 4,822,820 | 4/1989 | DeSantis et al. | 514/913 |
| 4,824,857 | 4/1989 | Goh et al. | 514/913 |
| 4,952,212 | 8/1990 | Booth et al. | 604/294 |
| 4,994,274 | 2/1991 | Chan et al. | 424/427 |
| 5,001,153 | 3/1991 | Ueno et al. | 560/121 |
| 5,011,856 | 4/1991 | Woodward | 514/573 |

OTHER PUBLICATIONS

Villumsen et al, "Prostaglandin F$_{2\alpha}$ Isopropylester Eye Drops: Effect on Introcular Pressure in Open-Angle Glaucoma", British Journal of Ophthamology; 1989, (Abstract only).

*Primary Examiner*—Randall L. Green
*Assistant Examiner*—Paul Prebilic
*Attorney, Agent, or Firm*—Robert J. Baran; Howard R. Lambert; Martin A. Voet

[57] ABSTRACT

The present invention relates to 2-decarboxyl-2-alkoxyalkyl prostaglandins that are potent ocular hypotentives, and are particularly suitable for the management of glaucoma. Said 2-decarboxyl-2-alkoxyalkyl prostaglandins are compounds of the formula (I)

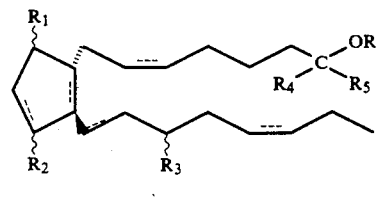

wherein the wavy line attachments indicate either alpha ($\alpha$) or beta ($\beta$) configuration; hatched lines indicate $\alpha$ configuration; solid triangles are used to indicate $\beta$ configuration; the dashed bonds represent a single bond or a double bond which can be in the cis or trans configuration; R is an aliphatic hydrocarbon group having from 1 to about 6 carbon atoms; one of $R_1$ and $R_2$ is =O, —OH or a —O(CO)R$_6$ group, and the other one is —OH or a —O(CO)R$_6$ group or $R_1$ is =O and $R_2$ is H, $R_3$ is —OH or —O(CO)R$_6$; $R_4$ and $R_5$ independently are hydrogen or an aliphatic hydrocarbon group having from 1 to about 6 carbon atoms; $R_6$ is a saturated or unsturated acyclic hydrocarbon group having from 1 to about 20 carbon atoms, or —(CH$_2$)$_n$R$_7$ wherein n is 0-10, and R$_7$ is an aliphatic ring from about 3 to about 7 carbon atoms or an aromatic or heteroaromatic ring; or a pharmaceutically acceptable salt of said compound.

The invention also provides a pharmaceutical product including a container adapted to dispense an ophthalmic solution in metered form and containing said 2-decarboxyl-2-alkoxyalkyl prostaglandin in admixture with a non-toxic, ophthalmically acceptable liquid vehicle.

21 Claims, 1 Drawing Sheet

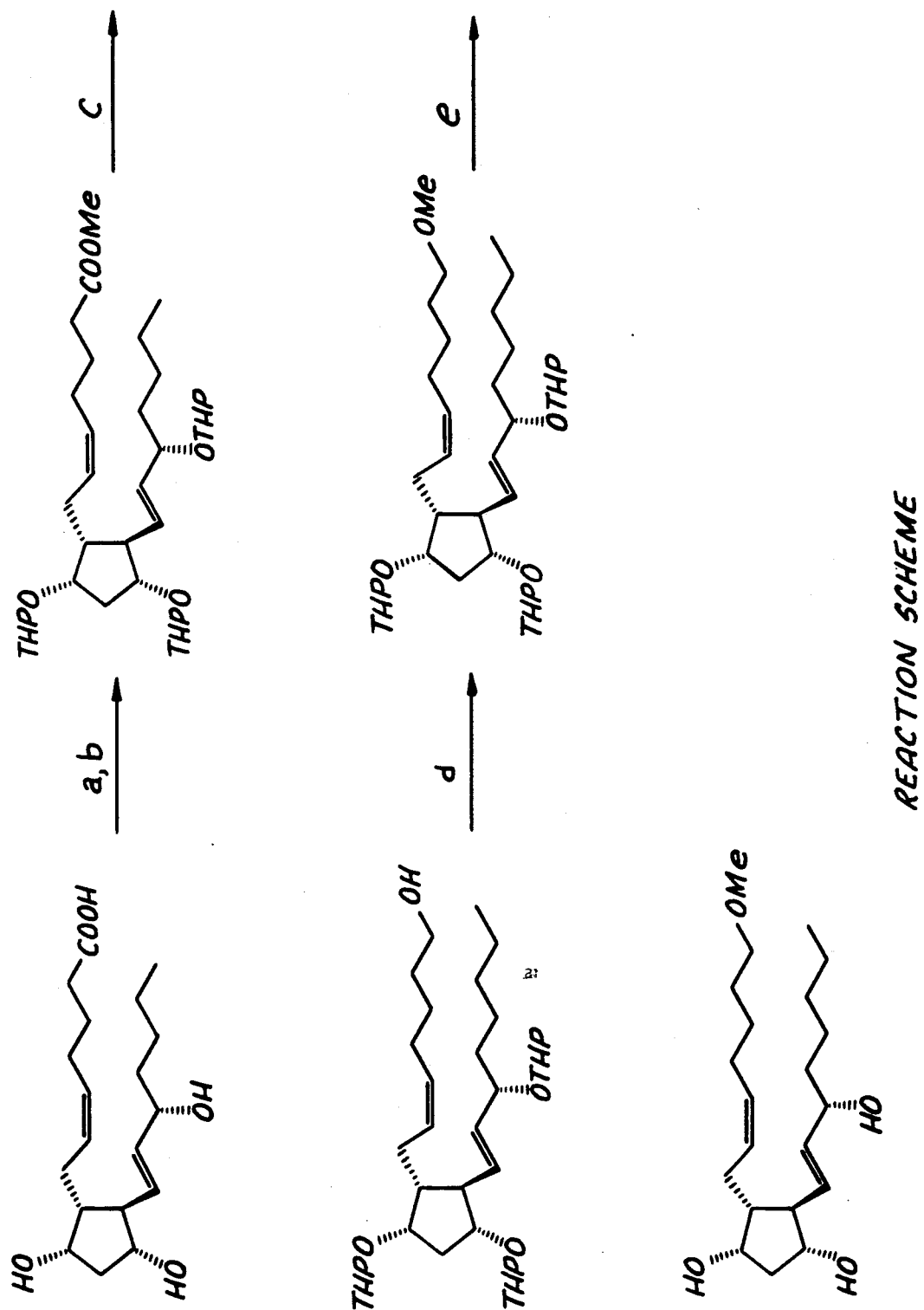
REACTION SCHEME

2-DECARBOXYL-2-ALKOXYALKYL PROSTAGLANDINS AS OCULAR HYPOTENSIVES

FIELD OF THE INVENTION

The present invention relates to 2-decarboxyl-2-alkoxyalkyl prostaglandins that are potent ocular hypotentives, and are particularly suitable for the management of glaucoma.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which has the following structural formula:

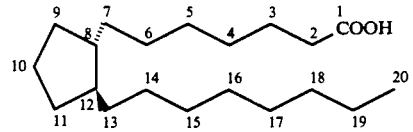

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\alpha}$)].

Prostaglandins were earlier regarded as potent ocular hypertensives, however, evidence accumulated in the last decade shows that some protaglandins are highly effective ocular hypotensive agents, and are ideally suited for the long-term medical management of glaucoma (see, for example, Bito, L. Z. *Biological Protection With Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28 (suppl), 284 (1987)].

The isopropyl ester of $PGF_{2\alpha}$ has been shown to have significantly greater hypotensive potency than the parent compound, presumably as a result of its more effective penetration through the cornea. In 1987 this compound was described as "the most potent ocular hypotensive agent ever reported" [see, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in p rticular $PGF_{2\alpha}$ and its prodrugs, e.g. its 1-isopropyl ester, in humans. The clinical potentials of prostaglandins in the management of conditions associated with increased ocular pressure, e.g. glaucoma are greatly limited by these side effects.

In a series of co-pending U.S. patent applications assigned to Allergan, Inc. prostaglandin esters with increased ocular hypotensive activity accompanied with no or substantially reduced side-effects are disclosed. The co-pending U.S. Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed May 25, 1989). Similarly, 11,15- 9,15- and 9,11-diesters of prostaglandins, for example 11,15-dipivaloyl $PGF_{2\alpha}$ are known to have ocular hypotensive activity. See the co-pending patent applications U.S. Ser. Nos. 385,645, 386,312 and 386,834 (all filed Jul. 27, 1989). PGF 1-alcohols are disclosed in the co-pending application U.S. Ser. No. 07/538,204, filed Jun. 14, 1990. The disclosures of all of these patent applications are hereby expressly incorporated by reference.

Prostan-1-ols and their esters are disclosed in the U.S. Pat. No. 4,256,745, as useful in triggering abortion or labor and in regulating the menstrual cycle in female mammals.

SUMMARY OF THE INVENTION

We have surprisinqly found that "ether-type" prostaglandin compounds, i.e. 2-decarboxyl-prostaglandins containing an alkoxyalkyl group in the 2-position, are more potent ocular hypotensives than $PGF_{2\alpha}$, and, unexpectedly, cause significantly less ocular surface hyperemia than the parent compounds.

In one aspect, the present invention relates to novel 2-decarboxyl-2-alkoxyalkyl prostaglandin derivatives of the formula (I)

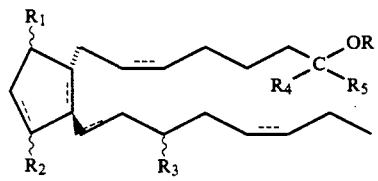

wherein the wavy line attachments indicate either alpha ($\alpha$) or beta ($\beta$) configuration; hatched lines indicate $\alpha$ configuration, solid triangles are used to indicate $\beta$ configuration; the dashed bonds represent a single bond or a double bond which can be in the cis or trans configuration; R is an aliphatic hydrocarbon group having from 1 to about 6 carbon atoms; one of $R_1$ and $R_2$ is =O, —OH or an —O(CO)$R_6$ group, and the other one is —OH or an —O(CO)$R_6$ group or $R_1$ is =O and $R_2$ is H; $R_3$ is —OH or —O(CO)$R_6$; $R_4$ and $R_5$ independently are hydrogen, or an aliphatic hydrocarbon group having from 1 to about 6 carbon atoms; $R_6$ is a saturated or unsaturated acyclic hydrocarbon group having from 1 to about 20 carbon atoms, or —(CH$_2$)$_n$R$_7$ wherein n is 0–10, and $R_7$ is an aliphatic ring from about 3 to about 7 carbon atoms, or an aromatic or heteroaromatic ring; or a pharmaceutically acceptable salt thereof.

In an other aspect, the present invention relates to pharmaceutical compositions for the treatment of ocular hypertension, comprising an amount sufficient to treat ocular hypertension of a compound of formula (I), wherein the symbols have the above meanings, in admixture with a non-toxic, ophthalmically acceptable carrier.

In a further aspect, the invention concerns a method of treating ocular hypertension which comprises applying to the eye an amount sufficient to treat ocular hypertension of a compound of formula (I), wherein the various symbols are as hereinabove defined.

In a still further aspect, the invention concerns ophthalmic solutions for the treatment of ocular hypertension, comprising an amount sufficient to treat ocular hypertension of a compound of formula (I), in admixture with a non-toxic, ophthalmically acceptable liquid vehicle, packaged in a container suitable for metered application.

In an-other aspect, the present invention relates to a pharmaceutical product, comprising:

a container adapted to dispense its contents in metered form; and an ophthalmic solution therein, as hereinabove defined.

DETAILED DESCRIPTION OF THE INVENTION

The present invention relates to ether derivatives of prostaglandins that are useful as ocular hypotensives. The prostaglandin derivatives used in accordance with the present invention are encompassed by the following structural formula (I)

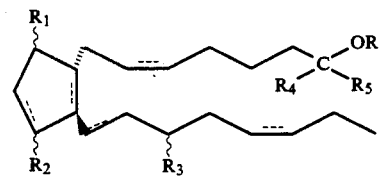

wherein the substituents and symbols are as herenabove defined.

The above formula includes 2-decarboxyl-2-alkoxyalkyl derivatives of prostaglandins of the F, D, E, A and B series. A preferred group of the compounds of the present invention is encompassed by the following formula (II)

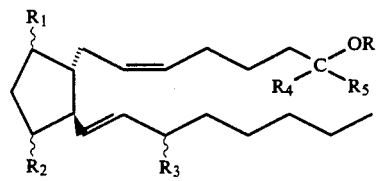

wherein $R_1/R_2$ is —OH/—OH, =O/—OH, —OH/=O and the esters of these compounds. This definition includes PGF, PGE and PGD derivatives.

Particularly preferred are the $PGF_{2\alpha}$ derivatives of the formula (III)

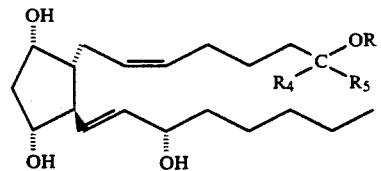

and their 9- and/or 11- and/or 15-esters.

In all of the above formulae, as well as in those provided hereinafter, the dotted lines on bonds between carbons 5 and 6 (C-5); between carbons 8 and 12 (C-8); between carbons 10 and 11 (C-10); between carbons 13 and 14 (C-13), and between carbons 17 and 18 (C-17) indicate a single or a double bond which can be in the cis or trans configuration. If two solid lines are used, that indicates a specific configuration for that double bond. Hatched lines at positions C-9, C-11 and C-15 indicate the $\alpha$ configuration. If one were to draw the $\beta$ configuration, a solid triangular line would be used.

The naturally occurring stereochemistry of $PGF_{2\alpha}$ includes the C-9, C-11, and C-15 hydroxyl groups in the $\alpha$ configuration. In the compounds used in accorance with the present invention, however, prostaglandins having the C-9 or C-11 or C-15 substituents in $\beta$ configuration are also contemplated. As hereinabove mentioned, in all formulas provided herein broken line attachments to the cyclopentane ring indicate substituents in the α configuration. Thickened solid line attachments to the cyclopentane ring indicate substituents in the β configuration. For instance, 9β-PGF compounds have the same structure as $PGF_\alpha$ compounds, except that the hydroxyl at the C-9 position is in the β configuration. Also, the broken line attachment of the hydroxyl group or other substituent to the C-11 and C-15 carbon atoms signifies the α configuration; therefore, compounds with the epi configuration for the hydroxyl group at C-15 are designated by using 15β and if there is no indication of the β configuration, the configuration is assumed α.

In the above formula the term "aliphatic hydrocarbon group" is used to refer to straight of branched chained, saturated or unsaturated acyclic hydrocarbon groups having from one to about 6, preferably one to about 4 carbon atoms. Such groups include alkyl, alkenyl and alkynyl groups of appropriate lenghts, and preferably are alkyl, e.g. methyl, ethyl, propyl, butyl, pentyl, or hexyl, or an isomeric form thereof.

The definition of $R_6$ may include a cyclic component, $-(CH_2)_nR_7$, wherein n is 0-10, $R_7$ is an aliphatic ring from about 3 to about 7 carbon atoms, or an aromatic or heteroaromatic ring. The "aliphatic ring" may be saturated or unsaturated, and preferably is a saturated ring having 3-7 carbon atoms, inclusive. As an aromatic ring, $R_7$ preferably is phenyl, and the heteroaromatic rings have oxygen, nitrogen or sulfur as a heteroatom. Preferably n is 0-4.

The most preferred compounds are those $PGF_{2\alpha}$ derivatives in which both R4 and R5 are hydrogen or one of $R_4$ and $R_5$ is hydrogen, and the other one is an aliphatic hydrocarbon group having from 1 to 6, preferably 1 to 4 carbon atoms. Particularly preferred are the compounds in which $R_4$ and $R_5$ both represent hydrogen, and R is lower alkyl, having from 1 to 4 carbon atoms. Most preferred are those compounds in which $R_4$ and $R_5$ are hydrogen, and R is methyl, the 2-decarboxyl-2-methoxymethyl compounds.

An especially preferred compound within the scope of the present invention is 2-decarboxyl-2-methoxymethyl $PGF_{2\alpha}$.

The 2-decarboxyl-2-alkoxyalkyl prostaglandins of the present invention can be conveniently prepared from the corresponding 2-decarboxyl-2-hydroxyalkyl prostaglandin derivatives. The primary alcohol starting compounds are prepared by reduction of the 1-carboxyl group of the corresponding PG compounds, for example, as described by Maddox et al., *Nature* 273, 549 (1978), or in the U.S. Pat. No. 4,256,745.

The secondary and tertiary alcohols are usually prepared from the corresponding primary alcohols via oxydation to aldehydes or ketones and subsequent reaction with a suitable Grignard reagent. These reactions are well known in the organic chemistry.

The prostaglandin 2-alcohols may be converted into the corresponding alkoxy derivatives by conventional techniques well known in the art for the preparation of ether-type compounds. For example, a prostaglandin-2-decarboxyl-2-ol starting compound can be reacted with the desired alkyl halide in a suitable organic solvent. During this step, the hydroxyl groups present in any of the 9-, 11- and 15-positions are protected by protecting groups known in the art, which can subsequently be easily removed.

A specific route for the synthesis of 2-decarboxyl-2-methoxymethyl-prostaglandin $F_{2\alpha}$ starting from $PGF_{2\alpha}$, is illustrated in the attached Reaction Scheme. In a first step, the methyl ester of $PGF_{2\alpha}$ is prepared with diazomethane, in a mixture of ether and methanol. The hydroxyls in the 9-, 11- and 15-positions are masked by reaction with dihydropyran, which yields tetrahydropyranyl (THP) ethers that are stable during the subsequent reduction and methylation steps, but can be easily decomposed with methanol, in the presence of pyridinium tosylate as a catalyst. The 1-carboxyl ester group of the obtained $PGF_{2\alpha}$ compound is reduced to the corresponding hydroxyl with diisobutylaluminium hydride. Other chemical reducing agents, including other hydrides, e.g., lithiumaluminium hydride may be equally used to perform this reaction. According to the Reaction Scheme, the methyl ester of the 2-OH compound is formed with methyl iodide, in the presence of sodium hydride, in dimethyl formamide solvent, at ambient temperature. In the final step, the THP protecting groups are removed to yield the desired 2-decarboxyl-2-methoxymethyl-$PGF_{2\alpha}$.

Pharmaceutical compositions may be prepared by combining a therapeutically effective amount of at least one compound according to the present invention, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples.

EXAMPLE 1

Preparation of 2-Decarboxyl-2-Methoxymethyl Prostaglandin F$_{2\alpha}$

PGF$_{2\alpha}$ (153 mg, 0.43 mmol) was dissolved in 2:1 methanol/methylene chloride (1.5 ml) and cooled to 0° C. A solution of diazoethane in ether was added until a yellow color persisted. The reaction was allowed to warm up to 25° C. and stirred for an additional 30 minutes. The solvents were evaporated to yield 158 mg of PGF$_{2\alpha}$ methyl ester as a yellow oil. The crude methyl ester was dissolved in methylene chloride (0.36 ml). 3,4-Dihydro-2H-pyran (0.40 ml, 4.3 mmol) and pyridinium P-toluenesulfonate (10 mg, 0.04 mmol) were added and the solution was stirred for 24 hours. The reaction mixture was partitioned between 10% citric acid and ethyl acetate and extracted with ethyl acetate. The organic extract was washed with saturated sodium bicarbonate solution and brine, dried over magnesium sulfate and concentrated to give 568 mg crude product. Purification by silica gel chromatography (40% ethyl acetate in hexanes, R$_f$ 0.60) afforded 401 mg PGF$_{2\alpha}$ tris(tetrahydropyranyl) ether methyl ester.

PGF$_{2\alpha}$ tris(tetrahydropyranyl) ether methyl ester obtained above was dissolved in methylene chloride, cooled to 0° C. and a solution of diisobutylaluminum hydride in methylene chloride (1.94 ml of 1.0M solution, 1.94 mmol) was added. After 45 minutes at 0° C., the reaction was quenched with 0.5M sodium hydroxide solution. The product was extracted into ethyl acetate, washed with brine and dried over anhydrous magnesium sulfate. The solvent was evaporated to give a crude product which was purified by column chromatography (silica gel, 30-40% ethyl acetate in hexanes, R$_f$ 0.15) to yield 219 mg PGF$_{2\alpha}$ 2- alcohol tris(tetrahydropyranyl) ether.

A solution of the purified alcohol from the above step (158 mg, 0.267 mmol) in dimethylformamide (0.5 ml) was added dropwise to a suspension of sodium hydride (16 mg of a 60% dispersion in mineral oil, 0.4 mmol) in dimethylformamide at 0° C. under a nitrogen atmosphere. The solution was warmed up to 25° C. for 15 minutes and recooled to 0° C. Methyl iodide (170 mg, 1.2 mmol) was added dropwise and the reaction was slowly warmed up to room temperature and stirred for an additional 28 hours. The reaction was worked up by adding 10% citric acid and extraction with ethyl acetate. The organic extract was washed with brine dried (magnesium sulfate) and concentrated to give 149 mg of crude product which was purified by column chromatography (silica gel, 30% ethyl acetate in hexanes, R$_f$ 0.38 to give 39 mg of 2-decarboxyl-2-methoxymethyl PGF$_{2\alpha}$ tris(tetrahydropyranyl) ether and 50 mg of starting material.

2-Decarboxyl-2-methoxymethyl PGF$_{2\alpha}$ tris (tetrahydropyranyl) ether (39 mg, 0.064 mmol) and pyridinium p-toluenesulfonate (10 mg) were dissolved in methanol (3 ml) and heated at 50° C. for 4 hours. The solvent was evaporated under reduced pressure. The residue was partitioned between water and ethyl acetate. The aqueous layer was further extracted with ethyl acetate twice and the combined organic extracts were washed with brine and dried over magnesium sulfate. On evaporation of the solvent, 21 mg crude product was obtained which was chromatographed on silica gel using 1% acetic acid in ethyl acetate as eluent (R$_f$, 0.33) to give 11 mg 2-decarboxyl-2-methoxymethyl PGF$_{2\alpha}$.

EXAMPLE 2

Intraocular Pressure Reducing Activity

Experimental quantities of PGF$_{2\alpha}$-2-OCH$_3$ (2-decarboxyl-2-methoxymethyl-PGF$_{2\alpha}$) were prepared in an ophthalmic formulation containing 0.1% polysorbate (Tween 80) - 10 mM TRIS. One eye of each experimental animal was treated by applying one 25 $\mu$l drop of the drug formulation to the ocular surface, the contralateral eye received 25 $\mu$l of vehicle as a control. Intraocular pressure was measured by applanation pneumatonometry immediately before drug administration and at subsequent, predetermined times thereafter. New Zealand albino/dutch belted cross rabbits were employed as experimental animals.

Ocular surface hyperemia was assessed by observation at predetermined times after drug administration and is described as either present or absent.

The effects of PGF$_{2\alpha}$-2-OCH$_3$ and PGF$_{2\alpha}$ on ocular hypertension and ocular surface hyperemia are summarized in Tables 1 and 2. The differences in activity are most clearly appreciated by comparing activities at the lowest dose (0.01%). Thus, PGF$_{2\alpha}$ caused only a modest decrease in intraocular pressure (−$), whereas the effect of PGF$_{2\alpha}$-2-OCH$_3$ produced significant decreases in intraocular pressure with a reduced incidence of ocular surface hyperemia. In the case of PGF$_{2\alpha}$, a similarly consistent separation of these two effects was not apparent.

TABLE 1

| PROSTANOID | (DOSE %) | 0 | 0.5 | 1 | 2 | 3 | 4 | 6 | 8 | 10 | 12 |
| --- | --- | --- | --- | --- | --- | --- | --- | --- | --- | --- | --- |

EFFECT ON INTRAOCULAR PRESSURE (mmiig)

TABLE 1-continued

| | | AT PREDETERMINED TIMES POST-ADMINISTRATION | | | | | | | | |
|---|---|---|---|---|---|---|---|---|---|---|
| PGF$_{2\alpha}$ | 0.01% | +0.7 | +0.4 | −0.4 | −2.3** | −1.3 | −0.25 | — | — | — |
| PGF$_{2\alpha}$ | 0.1% | +0.7 | +3.3* | −2.4 | −6.1** | −3.9* | −2.2** | −1.1 | | |
| PGF$_{2\alpha}$ | 1.0% | +7.9** | +8.7** | −1.2 | −7.2** | −7.0** | −10.3** | — | — | — |
| | | % ANIMALS EXHIBITING OCULAR SURFACE HYPEREMIA | | | | | | | | |
| PGF$_{2\alpha}$ | 0.01% | 100 | 100 | 100 | 100 | 50 | 12 | | | |
| PGF$_{2\alpha}$ | 0.1% | 100 | 100 | 100 | 100 | 100 | 75 | 0 | | |
| PGF$_{2\alpha}$ | 1% | 100 | 100 | 100 | 100 | 100 | 100 | | | |

TABLE 2

| PROSTANOID | (DOSE %) | 0 | 0.5 | 1.0 | 2.0 | 3.0 | 4.0 | 6.0 | 8.0 | 10.0 |
|---|---|---|---|---|---|---|---|---|---|---|
| | | EFFECT ON INTRAOCULAR PRESSURE (mmHg) AT PREDETERMINED TIMES POST-ADMINISTRATION | | | | | | | | |
| PGF$_{2\alpha}$2 OCH$_3$ | 0.01% | −3.8* | 0.25 | −2.7* | −3.6* | −4.2** | −2.7 | | | |
| PGF$_{2\alpha}$2 OCH$_3$ | 0.1% | — | +4.7* | −0.1 | −1.8 | −0.7 | −2.7 | | | |
| PGF$_{2\alpha}$2 OCH$_3$ | 1.0% | — | +12.1 | +6.1 | −2.1 | −2.8 | −7.8** | −7.7** | −5.4* | |
| | | % ANIMALS EXHIBITING OCULAR SURFACE HYPEREMIA | | | | | | | | |
| PGF$_{2\alpha}$2 OCH$_3$ | 0.01% | 66 | 100 | 100 | 50 | 33 | 0 | | | |
| PGF$_{2\alpha}$2 OCH$_3$ | 0.1% | — | 100 | 86 | 71 | 71 | 14 | | | |
| PGF$_{2\alpha}$2 OCH$_3$ | 1.0% | — | 100 | 100 | 100 | 100 | 87 | 33 | | |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

We claim:

1. A compound of the formula (I)

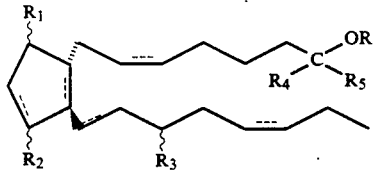

wherein the wavy line attachments indicate either alpha ($\alpha$) or beta ($\beta$) configuration; hatched lines indicate $\alpha$ configuration; solid triangles are used to indicate $\beta$ configuration; the dashed bonds represent a single bond or a double bond which can be in the cis or trans configuraton; R is an aliphatic hydrocarbon group having from 1 to about 6 carbon atoms; one of R$_1$ and R$_2$ is =O, —OH or a —O(CO)R$_6$ group, and the other one is —OH or —O(CO)R$_6$; R$_4$ and R$_5$ independently are hydrogen or an aliphatic hycrocarbon group having from 1 to about 6 carbon atoms; R$_6$ is a saturated or unsaturated acyclic hydrocarbon group having from 1 to about 20 carbon atoms, or —(CH$_2$)$_n$R$_7$ wherein n is 0–10, and R$_7$ is an aliphatic ring from about 3 to about 7 carbon atoms or an aromatic or heteroaromatic ring; or a pharmaceutically acceptable salt of said compound.

2. The compound according to claim 1 selected from the group consisting of naturally occurring prostaglandins of the D, E and F series.

3. The compound according to claim 2 having the formula (II)

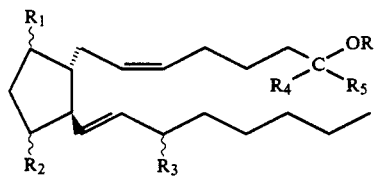

wherein R, R$_3$, R$_4$ and R$_5$ are as defined in claim 1, and R$_1$/R$_2$ is —OH/—OH, =O/—OH, —OH/=O, or an ester thereof wherein any —OH may be replaced with —O(CO)R$_6$.

4. The compound according to claim 3 which is a PGF$_{2\alpha}$ derivative of the formula (III)

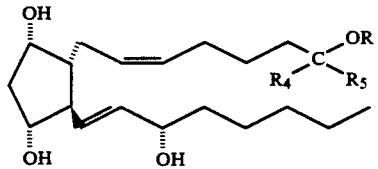

wherein R, R$_4$ and R$_5$ are as defined in claim 1.

5. The compound according to claim 4, in which R is alkyl having from 1 to 6 carbon atoms, and both R$_4$ and R$_5$ are hydrogen.

6. The compound according to claim 5, in which said compound is 2-decarboxyl-2methoxymethyl PGF$_{2\alpha}$.

7. A pharmaceutical composition for the treatment of ocular hypertension, said composition comprising an amount sufficient to treat ocular hypertension of a compound of formula (I)

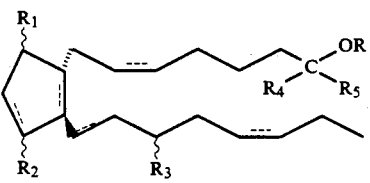

wherein the wavy line attachments indicate either alpha (α) or beta (β) configuration; hatched lines indicate α configuration; solid triangles are used to indicate β configuration; the dashed bonds represent a single bond or a double bond which can be in the cis or trans configuration; R is an aliphatic hydrocarbon group having from 1 to about 6 carbon atoms; one of $R_1$ and $R_2$ is =O, —OH or a —O(CO)$R_6$ group, and the other one is —OH or a —O(CO)$R_6$ group or $R_1$ is =O and $R_2$ is H; $R_3$ is —OH or —O(CO)$R_6$; $R_4$ and $R_5$ independently are hydrogen or an aliphatic hydrocarbon group having from 1 to about 6 carbon atoms; $R_6$ is a saturated or unsaturated acyclic hydrocarbon group having from 1 to about 20 carbon atoms, or —(CH$_2$)$_n$R$_7$ wherein n is 0–10, and $R_7$ is an aliphatic ring from about 3 to about 7 carbon atoms or an aromatic or heteroaromatic ring; or a pharmaceutically acceptable salt of said compound.

8. The composition according to claim 7 wherein said compound is selected from the group consisting of naturally occurring prostaglandins of the D, E and F series.

9. The composition according to claim 8 wherein said compound has the formula (II)

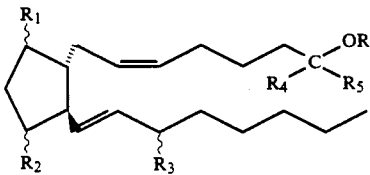

wherein R, $R_3$, $R_4$ and $R_5$ are as defined in claim 7, and $R_1/R_2$ is —OH/—OH, =O/—OH, —OH/=O, or an ester thereof wherein any —OH may be replaced with —O(CO)$R_6$.

10. The composition according to claim 9 wherein said compound is PGF$_{2\alpha}$ derivative of the formula (III)

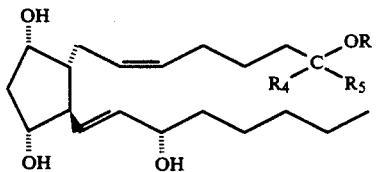

wherein R, $R_4$ and $R_5$ are as defined in claim 7.

11. The composition according to claim 10, in which R is alkyl having from 1 to 6 carbon atoms, and both $R_4$ and $R_5$ are hydrogen.

12. The composition according to claim 11, in which R is methyl, and $R_4$ and $R_5$ are hydrogen, 2-decarboxyl-2-methoxymethyl PGF$_{2\alpha}$.

13. A method of treating ocular hypertension which comprises applying to the eye a pharmaceutical composition, said composition comprising an amount sufficient to treat ocular hypertension of a compound of formula (I)

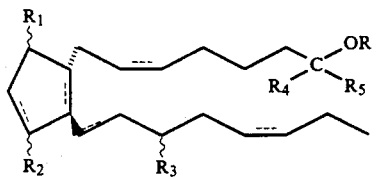

wherein the wavy line attachments indicate either alpha (α) or beta (β) configuration; hatched lines indicate α configuration; solid triangles are used to indicate β configuration; the dashed bonds represent a single bond or a double bond which can be in the cis or trans configuration; R is an aliphatic hydrocarbon group having from 1 to about 6 carbon atoms; one of $R_1$ and $R_2$ is =O, —OH or a —O(CO)$R_6$ group, and the other is —OH or a —O(CO)$R_6$ group or $R_1$ is =O and $R_2$ is H; $R_3$ is —OH or —O(CO)$R_6$; $R_4$ and $R_5$ independently are hydrogen or an aliphatic hydrocarbon group having from 1 to about 6 carbon atoms; $R_6$ is a saturated or unsaturated acyclic hydrocarbon group having from 1 to about 20 carbon atoms, or —(CH$_2$)$_n$R$_7$ wherein n is 0–10, and $R_7$ is an aliphatic ring from about 3 to about 7 carbon atoms or an aromatic or heteroaromatic ring; or a pharmaceutically acceptable salt of said compound.

14. The method according to claim 13 wherein said compound is selected from the group consisting of naturally occurring prostaglandins of the D, E and F series.

15. The method according to claim 14 wherein said compound has the formula (II)

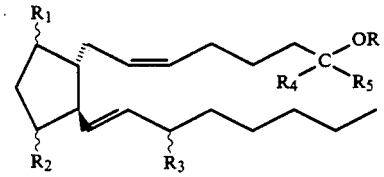

wherein R, $R_3$, $R_4$ and $R_5$ are as defined in claim 13, and $R_1/R_2$ is —OH/—OH, =O/—OH, —OH/=O, or an ester thereof wherein any —OH may be replaced with —O(CO)$R_6$.

16. The method according to claim 15 wherein said compound is a PGF$_{2\alpha}$ derivative of the formula (III)

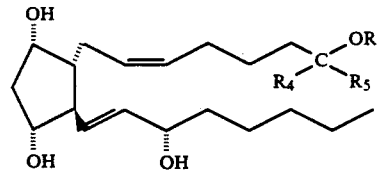

wherein R, $R_4$ and $R_5$ are as defined in claim 13.

17. The method according to claim 16, wherein R is alkyl having from 1 to 6 carbon atoms, and both $R_4$ and $R_5$ are hydrogen.

18. The method according to claim 17, in which said compound is 2-decarboxyl-2-methoxymethyl PGF$_{2\alpha}$.

19. A pharmaceutical product comprising an opthalmic solution for the treatment of ocular hypertension, said solution comprising an amount sufficient to treat ocular hypertension of a compound of formula (I) according to claim 1, in admixture with a non-toxic, ophthalmically acceptable liquid vehicle, packaged in a container suitable for metered application.

20. The product according to claim 19, wherein said compound is a PGF$_{2\alpha}$ derivative.

21. The product according to claim 20 wherein said PGF$_{2\alpha}$ derivative is 2-decarboxyl-2-methoxymethyl PGF$_{2\alpha}$.

* * * * *

UNITED STATES PATENT AND TRADEMARK OFFICE
CERTIFICATE OF CORRECTION

PATENT NO. : 5,139,491
DATED : August 18, 1992
INVENTOR(S) : MING FAI CHAN AND DAVID F. WOODWARD It is certified that error appears in the above-indentified patent and that said Letters Patent is hereby corrected as shown below:

In column 9, line 63, after "- $O(CO)R_6$" add --group or $R_1$ is = O and $R_2$ is H; $R_3$ is - OH or -$O(CO)R_6$ --.

In column 9, line 63, after "or" insert --a--.

Signed and Sealed this

Seventh Day of December, 1993

Attest:

BRUCE LEHMAN

Attesting Officer   Commissioner of Patents and Trademarks